United States Patent
Jung et al.

(10) Patent No.: US 10,039,683 B2
(45) Date of Patent: Aug. 7, 2018

(54) COMPRESSION BANDAGE FOR PLACING ON THE HUMAN OR ANIMAL BODY

(75) Inventors: Harald Jung, Kreimbach-Kaulbach (DE); Michael Kloeppels, Aachen (DE)

(73) Assignee: KARL OTTO BRAUN GMBH & CO. KG, Wolfstein (DE)

( * ) Notice: Subject to any disclaimer, the term of this patent is extended or adjusted under 35 U.S.C. 154(b) by 160 days.

(21) Appl. No.: 14/118,763

(22) PCT Filed: May 2, 2012

(86) PCT No.: PCT/EP2012/058023
§ 371 (c)(1),
(2), (4) Date: Nov. 19, 2013

(87) PCT Pub. No.: WO2012/163616
PCT Pub. Date: Dec. 6, 2012

(65) Prior Publication Data
US 2014/0107544 A1    Apr. 17, 2014

(30) Foreign Application Priority Data
May 27, 2011    (DE) .......................... 10 2011 076 596

(51) Int. Cl.
*A61F 13/00*    (2006.01)
*A61H 1/00*    (2006.01)
(Continued)

(52) U.S. Cl.
CPC ............. *A61H 1/008* (2013.01); *A61F 13/00* (2013.01); *A61F 13/0273* (2013.01); *A61F 13/06* (2013.01)

(58) Field of Classification Search
CPC ................. A61F 13/00; A61F 13/0273; A61F 2013/00102; A61F 2013/00119;
(Continued)

(56) References Cited

U.S. PATENT DOCUMENTS 1,528,882 A * 3/1925 Kennerly ................ A41F 15/02
                                                              2/337
3,409,008 A * 11/1968 Mortensen ........ A61F 13/00021
                                                              139/421
(Continued)

FOREIGN PATENT DOCUMENTS

CN    2075080 U    4/1991
CN    2171604 Y    7/1994
(Continued)

OTHER PUBLICATIONS

International Search Report issued by the European Patent Office in International Application PCT/EP2012/058023 dated Jun. 25, 2012.

*Primary Examiner* — Kari Rodriquez
(74) *Attorney, Agent, or Firm* — Henry M. Feiereisen LLC

(57) ABSTRACT

A compression bandage for placing on the human or animal body, includes a planar sheet material with a longitudinal direction and a transverse direction, and two transverse edges lying opposite each other in the longitudinal direction, and two longitudinal edges lying opposite each other in the transverse direction, wherein the sheet material is made of a fabric with a warp and a weft system of threads, wherein at least one of the thread systems includes elastic threads, wherein the thread density in the warp and/or weft system of threads is varied in the longitudinal direction of the bandage such that at least one section of the bandage in the longitudinal direction has a warp and/or weft thread density different than an adjacent section.

9 Claims, 4 Drawing Sheets

(51) Int. Cl.
*A61F 13/02* (2006.01)
*A61F 13/06* (2006.01)

(58) Field of Classification Search
CPC .. A61F 2013/00131; A61F 2013/00144; A61F 2013/00148; D03D 15/08; D03D 15/04; D03D 7/00; D03D 13/008; D03D 2700/0103
See application file for complete search history.

(56) References Cited

U.S. PATENT DOCUMENTS

| | | | |
|---|---|---|---|
| 4,207,885 A * | 6/1980 | Hampton | A61F 13/00021 139/419 |
| 4,640,317 A | 2/1987 | Chardon | |
| 4,699,133 A * | 10/1987 | Schafer | A61F 13/00987 427/208.6 |
| 5,195,950 A | 3/1993 | Delannoy | |
| 5,507,682 A * | 4/1996 | Grahammer | A41F 15/005 139/421 |
| 6,860,865 B1 | 3/2005 | Feldgiebel | |
| 7,886,776 B2 | 2/2011 | Jung et al. | |
| 2010/0093258 A1* | 4/2010 | Glenn | A41F 15/00 450/86 |
| 2011/0191937 A1* | 8/2011 | Wang | A42C 5/02 2/181 |
| 2011/0224594 A1* | 9/2011 | Mueller | A61F 13/062 602/75 |

FOREIGN PATENT DOCUMENTS

| | | |
|---|---|---|
| DE | 2 240 945 | 2/1974 |
| DE | 102005033720 | 1/2007 |
| EP | 0 490 793 | 6/1992 |
| FR | 2 433 935 | 3/1980 |
| GB | 680670 | 10/1952 |
| JP | S60-110951 | 7/1985 |
| JP | 04-018512 | 1/1992 |
| JP | H06272103 | 9/1994 |
| WO | WO 98/47452 | 10/1998 |
| WO | WO 99/56683 | 11/1999 |
| WO | WO 2007/009625 | 1/2007 |

* cited by examiner

COMPRESSION BANDAGE FOR PLACING ON THE HUMAN OR ANIMAL BODY

CROSS-REFERENCES TO RELATED APPLICATIONS

This application is the U.S. National Stage of International Application No. PCT/EP2012/058023, filed May 2, 2012, which designated the United States and has been published as International Publication No. WO 2012/163616 and which claims the priority of German Patent Application, Serial No. 10 2011 076 596.4, filed May 27, 2011, pursuant to 35 U.S.C. 119(a)-(d).

BACKGROUND OF THE INVENTION

The invention relates to a compression bandage for application to the human or animal body including a planar sheet material with a longitudinal direction and a transverse direction and two transverse edges which oppose each other in the longitudinal direction and two longitudinal edges which oppose each other in the transverse direction, wherein the sheet material consists of a fabric with a warp thread system and a weft thread system, wherein at least one of the thread systems includes elastic threads. Compression bandages are amply known in the state of the art.

For example, woven and knitted bandages are used in adhesive and also non-adhesive form, and are applied in particular in the treatment of various venous conditions. Conventional elastically woven or knitted bandages have a warp thread and a weft thread system, wherein in particular the warp threads are configured elastic. In this regard it is important that the bandages are applied with the correct tension in order to maintain a desired compression force underneath the bandage. Thus, bandages are used in the compression therapy, which have a predetermined stretchability over their entire length and are applied on a leg from distal to proximal over the heel, the ankle region, the shin and as the case may be also the knee and the upper leg. Problems arise in this context due to the different geometries of the wrapped round regions, the differences regarding application and the compression effect. Corresponding bandages must ensure a certain minimal compression pressure over the entire bandage.

In conventional configurations of such a compression bandage, difficulties may arise during application for example in the heel area, and the different geometries of the areas to be wrapped cannot sufficiently be taken into account.

This leads to different compression effects, which cannot be changed or influenced in specific sites or sections. Therefore, in order to take the differences of the regions to be wrapped into account to date bandages with different widths are offered. These are single bandages and also combination packs with bandages of different width, which are wrapped successively or on top of each other.

In addition WO 98/47452 discloses a compression bandage made of a woven or knitted elastic bandage material for application on a body part, wherein a guiding line for application is provided which does not extend parallel to at least one edge of the bandage. In particular, the bandage is to be configured trapeze-shaped from an end arranged in longitudinal direction to a further end which is spaced apart therefrom in longitudinal direction, wherein the narrower end is applied on a limp so that it comes to lie at the location where the higher compression force is needed, for example in the region of the ankle, and the wider region of the bandage is for example applied in the calf area where a smaller compression force is to be provided.

SUMMARY OF THE INVENTION

The object of the present invention is to provide a compression bandage, which during application takes the different dimensions and geometries of a limp and the different compression force, which is applied to the different areas of a limp into account.

The invention solves this objet with a compression bandage in which the density of the threads in the warp and/or weft thread system is varied in the longitudinal direction of the bandage so that at least one section along the longitudinal direction of the bandage has a different warp and/or weft thread density than a neighboring section.

Compared to a bandage conventionally used in the compression therapy, which has the same properties over its entire length, the present configuration allows taking into account differences resulting from the different geometries of the wrapped round regions, the application properties and the compression effect. For example, bandages can be produced which in their longitudinal direction have properties that are adjusted to the different leg areas by providing different densities of warp or weft threads in at least two regions that neighbor each other in longitudinal direction. In this way the application properties and the effect of the compression bandage can be improved.

The mass per area of the bandage or bandage and the stretchability and compression force can be adjusted via the variation of the warp thread and/or weft thread density, wherein a minimal compression force can be ensured over the entire bandage.

In particular, the properties oft the bandage with regard to the three aforementioned parameters are variably adjustable and individually adaptable over the length of the bandage. This allows achieving an improved application property and the compression pressure can be adjusted at specific sites over the length of an extremity to be wrapped. It is conceivable to adjust bandages individually for each patient based on measurements of the extremities.

It is provided that by varying the number of the warp and/or weft threads in a warp thread or weft thread system, the warp thread density or the weft thread density, i.e., the number of threads per centimeter bandage width or bandage length is varied.

It can also be provided that the warp threads are configured elastic whereas the weft threads are configured non-elastic. As an alternative, the warp threads and the weft threads can be elastic so that a bi-elastic bandage, which is elastic in longitudinal and transverse direction is generated. Particularly preferred is that the elastic threads are cotton elastic threads, wherein in particular cotton crepe threads can be used.

The stretchability of the bandage or bandage can be controlled and calculated within certain ranges via the weft thread density or via the thickness of the weft yarns.

Overwound cotton yarns or twines allow adjusting the desired stretchability and compression force. The overwound twines or yarns, preferably made of cotton, give off their excessive energy in the fabric in that they shorten as a result of treatment with water and tensides and are thereby elastified.

Cotton elastic crepe threads significantly influence the effectiveness of compression bandages. In particular, cotton elastic crepe threads result in a finished sheet with low
} resting pressure at desired working pressure due to their textile design and their textile construction.

In addition, permanently elastic or durably elastic materials in combination with other yarn and/or fiber types can be used. For example texturized thermoplastic materials can be used as they are known in the state of the art in durably elastic long-stretch bandages or in permanently elastic bandages for example in the bandage "Lastodur straff" of the Paul Hartmann company AG Heidenheim, Germany.

Warp threads are threads which extend in longitudinal direction of the bandage, wherein weft threads are the threads that extend transversely thereto.

The terms bandage and bandage are to be used synonymously.

It is particularly preferred when the warp thread density of two sections that are adjacent in longitudinal direction is different at same weft thread density. As an alternative, the inverse configuration can be provided, i.e., the weft thread density of two sections that are spaced apart in longitudinal direction can be different at same warp thread density. The additional variation of the weft thread density allows controlling the stretching in order to further adjust the compression pressure as desired. Generally however, the warp and the weft thread density can both be varied in particular in different and/or same sections of the bandage.

As a result of increasing the density in the warp thread region in a longitudinal bandage an increase of the compression force is achieved, This is for example desirable in the region of the ankle and in the lower region of the wade. Because the increase in density does not occur abruptly, a compression force reduction from distal to proximal is already achieved by the changed warp thread density in the weave. When simultaneously reducing the weft density the stretchability can be increased and when increasing the weft density the stretchability decreased.

Particularly preferably, the sections of different thread densities can have a different extent in thickness direction. In particular the regions with lower warp thread density can have a greater width than the regions with greater warp thread density. In this way the density can be varied while leaving the number of threads for example the warp threads the same.

In addition, the compression bandage can have further layers, in particular adhesive layers can be provided which are in particular disposed on the fabric of the sheet material in the form of a bonding coating. The bonding coating can be of adhesive as well as purely cohesive nature, i.e., only configured so that it adheres onto itself but not on skin and hairs or the garments of the wearer.

In particular it is provided that more than two sections of different warp thread or weft thread density are provided. It can in particular be provided that two regions of lower warp thread density and/or weft thread density enclose a region of higher warp thread density and/or weft thread density. When the extent of the bandage in width direction is also varied along with varying the thread density, this can be done in such a way so that within the regions of constant thread density the longitudinal edges which oppose each other in transverse direction are configured substantially parallel and a narrowing or widening occurs only at the transition from one thread density to the next thread density so that a trapeze-shaped section of the compression bandage is formed.

A particularly preferred embodiment is a short-stretch bandage with alternating width and compression pressure, wherein here in a region of lower warp thread density and/or weft thread density end regions of eh bandage are provided respectively in the longitudinal direction and between the end regions a region with higher warp thread density and/or weft thread density. The regions with different warp thread density can be congruent with the regions of different weft thread density, however, they may also not or only partially overlap with each other.

Further, the ratio of the warp thread density of the region with lower warp thread density to the warp thread density of the region with greater warp thread density can be 4:5, in particular from 170 to 220 threads per 10 cm and in particular from 172 to 192 threads per 10 cm.

The ratio of the weft thread density of the region with lower weft thread density to the weft thread density of the region with the greater weft thread density can be from 8.0 to 1.2, in particular from 130 to 180 threads per 10 cm, and in particular from 140 to 150 threads per 10 cm.

Finally it can preferably be provided that the compression bandage has on at least one side of the planar sheet material a coating in particular a cohesive or adhesive coating.

A corresponding short-stretch bandage can be configured as follows:

EXAMPLE 1

Varying Warp Thread Density

Part 1 and part 3 of the bandage in longitudinal direction
Materials: cotton crepe thread, 25 tex×2 T/N ca. 2000 S+Z
Warp thread number: 86 threads. −S+86 threads−Z
Warp pattern repeat: 2S−2Z
Warp density in cm: 17.2
Bandage width: 10 cm
Compression pressure at 50% stretching and two layered wrapping
Leg diameter: 12 cm 27 mm hg
Part 2 (between part 1 and 3) of the bandage in longitudinal direction
Materials: cotton crepe thread, 25 tex×2 T/N ca. 2000 S+Z
Warp thread number: 86 threads−S+86 threads
Warp pattern rapport: 2S=2Z
Warp density in cm: 215
Bandage width: 8 cm
Compression pressure at 50% stretching and two layered wrapping
Leg diameter: 12 cm
Compression pressure: 34 mm Hg
Length of the bandage in part 1 and part 3: ca. 3 m stretched
Length of the bandage in part 2: ca. 2 m stretched.

EXAMPLE 2

Varying Weft Thread Density in Longitudinal Direction of the Bandage

For all sections in longitudinal direction:
Bandage length: 10 cm
Material: cotton thread of the strength 36 tex, single
Weft thread density in section 1 and 3 (before and after weft thread density change):
146 threads per 10 cm
Compression pressure at 50% stretching and two-layered wrapping and a leg diameter of 12 cm: 27 mm Hg
Weft thread density in section 2 (while weft thread density change and between the sections 1 and 3): 180 threads per 10 cm Compression pressure at 50% stretching and two-layered wrapping and a leg diameter of 12 cm: 33 mm Hg.

EXAMPLE 3

Variation of Warp and Weft Thread Density in a Section

For all length sections:
Material warp threads: cotton crepe thread, 25 tex×2 T/N ca. 2000 S+Z
Material weft threads: cotton threads 36 tex×1
Warp pattern repeat: 86 threads S+86 threads Z
Length section part 1 and part 3 (before and after warp and weft thread density change, in longitudinal direction of the bandage):
Bandage width 10 cm
Warp thread density: 172 threads per 10 cm
Weft thread density: 146 threads per 10 cm
Compression pressure at 50% stretching and two layered wrapping and a leg diameter of 12 cm: 27 mm Hg
Length section part 2 (during warp and weft thread density change, between part 1 and 3):
Bandage width 215 threads per 10 cm
weft thread density 180 threads per 10 cm
Compression pressure at 50% stretching and two layered wrapping and a leg diameter of 12 cm: 41 mm Hg Such bandages are woven on an electronically controlled power loom with different blade width and blade densities. The equipment and confectioning occurs continuously at endless bands. The above specifications for a preferred embodiment of such a compression bandage show how the compression pressure can be varied by adjusting the warp thread number per cm by changing the bandage width. The compression pressure that can be generated with the bandage can be measured as resting pressure in vivo at the resting, lying human leg with a pressure measuring device of the company Kikuhime. For this the pressure sensor of the pressure measuring device is placed between angled bandage and the skin at the transition from the Achilles tendon to the soleus muscle (corresponds to the measuring point B1 defined in the norm RAL GZ 387) and two bandages are wrapped on top of each other in circular wrapping with four layers lying on top of each other over the pressure sensor.

BRIEF DESCRIPTION OF THE DRAWING

In the following, the invention is explained in more detail by way of a drawing. It is shown in.

DETAILED DESCRIPTION OF PREFERRED EMBODIMENTS

Figure 1:
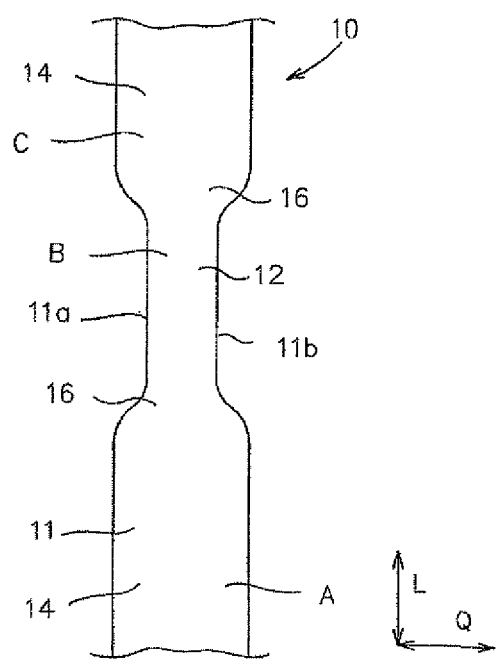
FIG. 1 a section of a compression bandage according to the invention
FIG. 2 a strongly schematized representation of two regions of a bandage according to the invention with different warp thread density.

FIG. 1 shows a section of a compression bandage according to the invention including a planar sheet material 11 with a longitudinal direction L and transverse direction Q and two longitudinal edges 11a and 11b and two not shown also opposing transverse edges.

The warp threads in this case are configured elastic in particular cotton elastic. The weft threads are non-elastic. The bandage is divided into essentially three sections A, B, C, wherein a section B with higher warp thread density 12 is enclosed by two sections A, C with lower warp thread density 14. The sections A, B, and C adjoin each other in longitudinal direction L. The longitudinal edges 11a, 11b which in longitudinal direction L of the bandage 10 oppose one another in transverse direction, are arranged substantially parallel to each other in the region of the sections A, B, C. In the region of the transition from a section A, C with low warp thread density 14 to a section B with high warp thread density 12 the bandage 10 narrows or widens so that here trapeze-shaped regions 16 are generated.

The variation of the bandage width at same number of warp threads results in a change of the warp thread density.

When applying the bandage for example onto a human leg, a higher compression force can be achieved in the region B of the bandage 10 than in the regions A and C. In addition, the different bandage width beside the higher compression force associated therewith also enables an easier application on areas of the human body that strongly deviate from the cylindrical or conical shape such as the foot or ankle region.

Different width bandages 10 which have to be combined with each other are not required.

Figure 2:
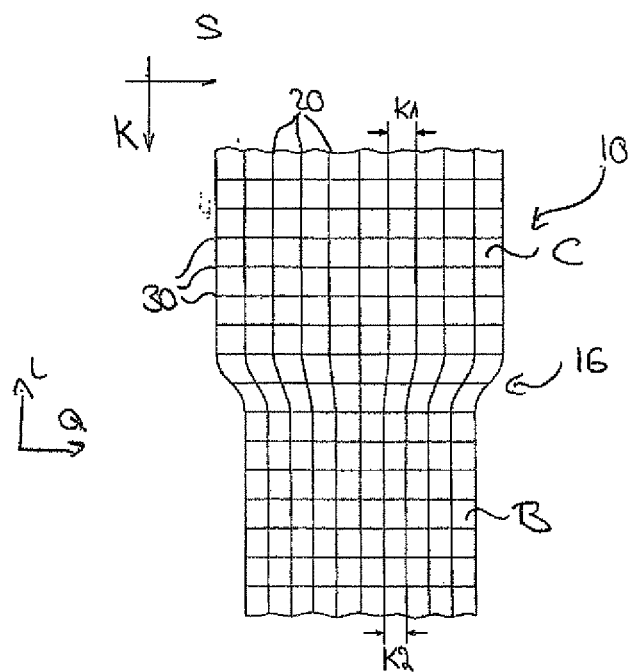

FIG. 2 shows a section of the bandage 10 from the regions C and B and the transition region 16. The warp threads are designated with reference numeral 20 and the weft threads with reference numeral 30. The weft direction is designated with the letter S and the warp direction with the letter K. The density of the weft threads 30 remains constant over the entire length L of the bandage, wherein the density of the warp threads 20 from the section C with lower warp thread density 14 to the section B with higher warp thread density is increased in that the bandage width in transverse direction Q in the section B is lower than in the section C. this results in a transition region 16 which is substantially trapeze-shaped and continuously narrows starting from the region C to the region B. The warp threads have the distance K1 in the region C, wherein in the region B the distance of the warp threads is K2 and K2 is smaller than K1.

Figure 3:
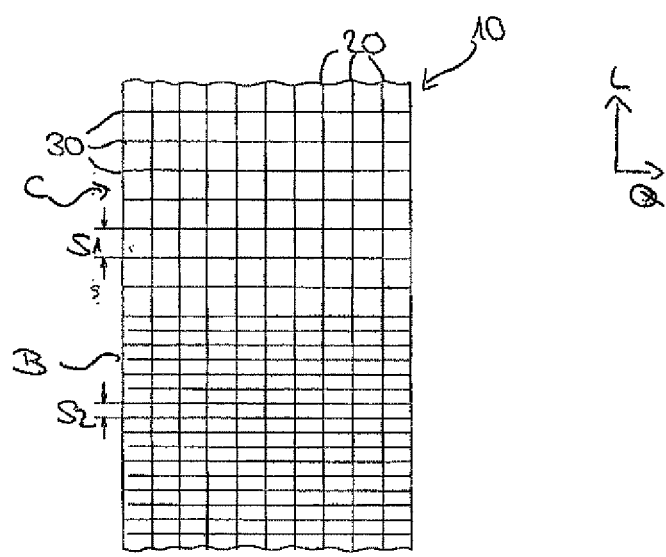
FIG. 3 a strongly schematized representation of two bandage regions of a bandage according to the invention with different weft thread density and
FIG. 4 a strongly schematized representation of two regions with different warp and weft thread density.

FIG. 3 shows a configuration in which the density and with this the distances of the warp threads 20 remains constant over the entire length L of the bandage 10 and the density of the weft threads 30 changes over the length L, wherein the distance of the weft threads 30 in the region which is also designated C is designated with S1 and in the region which is designated also as B and has a lower weft thread density with S2. Wherein S2<S1. The bandage has in this case the same width Q over the entire length. While the compression force can be adjusted via varying the warp thread density, the stretchability is varied by varying the weft thread density. In addition, variation of the weft thread density causes change of the mass per are of the bandage from a region with lower density C to a region with higher density B.

Figure 4:
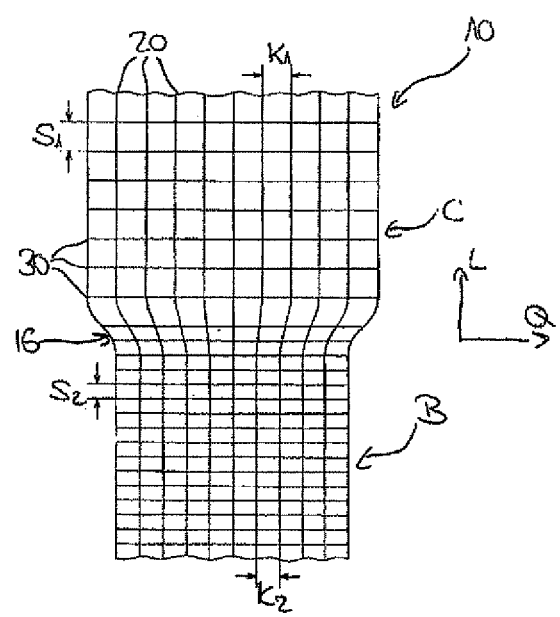

Finally, FIG. 4 shows an embodiment in which starting from a region B with lower weft and warp thread density to a region C which has a higher warp and weft thread density both thread systems are varied with regard to their density. Thus, in the region C the bandage 10 has a distance K1 between the warp threads and a distance of two warp threads to each other of S1, wherein in the region B which has a higher warp and weft thread density the weft threads have the distance S2 and the warp threads have a distance K2. S2 is smaller than S1 and K2 smaller than K1.

Also in this case the variation of the warp thread density from a distance K1 to a distance K2 is achieved by narrowing the bandage in transverse direction Q so that a transition region 16 is formed which again has a narrowing shape starting from the region C to the region B.

By varying the warp and also the weft thread systems regarding their density, all free parameters can be adjusted as desired and a bandage can be produced which can be individually and optimally adjusted to the given situation, if desired also to a wearer.

Further embodiments of the invention become apparent form the remaining application material.

The invention claimed is:

1. A compression bandage for application on a human or animal body, comprising a planar sheet material having a longitudinal direction and a transverse direction, two transverse edges opposing each other in the longitudinal direction and two longitudinal edges opposing each other in the transverse direction, said planar sheet material being made of a fabric having a warp and a weft thread system, wherein at least one of the warp and the weft thread systems includes cotton elastic threads, wherein a thread density in at least one of the warp and the weft thread system varies along the longitudinal direction of the bandage so that in at least one section of the bandage a distance between warp threads and/or a distance between weft threads is different than in another section of the bandage directly adjacent the at least one section in the longitudinal direction, wherein at least one side of the planar sheet material has a cohesive coating configured to adhere onto itself but not on skin and hairs or a garment of a wearer.

2. The compression bandage of claim 1, wherein a warp thread density of the at least one section and the other section differs, and wherein a weft thread density of the at least one section and the another section is the same.

3. The compression bandage of claim 1, wherein a weft thread density of the at least one section differs from a weft thread density of the other section, and wherein a warp thread density of the at least one section and the another section is the same.

4. The compression bandage of claim 1, wherein a weft thread density and a warp thread density of the at least one section differ from a weft thread density and a warp thread density of the another section.

5. The compression bandage of claim 1, wherein the at least one section and the another section have different respective extents in the transverse direction.

6. The compression bandage of claim 1, wherein a ratio between a warp thread density of the at least one section and a warp thread density of the another section is 4:5.

7. The compression bandage of claim 6, wherein the at feast one section has a warp thread density of 170 to 220 threads per 10 cm.

8. The compression bandage of claim 6, wherein the at least one section has a warp thread density of 172 to 190 threads per 10 cm.

9. The compression bandage of claim 1, wherein a ratio between a weft thread density of the at least one section and a weft thread density of the another section is 0.8 to 1.2.

* * * * *